United States Patent [19]

Haardt et al.

[11] Patent Number: 5,141,732
[45] Date of Patent: Aug. 25, 1992

[54] PROCESS FOR THE REMOVAL OF AMMONIUM SULPHATE FROM TARRICH WASTE STREAMS FROM THE PRODUCTION OF (METH) ACRYLONITRILE

[75] Inventors: Hans-Jürgen Haardt, Pulheim; Jens Herwig, Cologhe; Ernst-Friedrich Neeb, Dormagen, all of Fed. Rep. of Germany

[73] Assignee: EC Erdolchemie GmbH, Cologne, Fed. Rep. of Germany

[21] Appl. No.: 683,500

[22] Filed: Apr. 4, 1991

Related U.S. Application Data

[63] Continuation of Ser. No. 466,174, Jan. 17, 1990.

[30] Foreign Application Priority Data

Feb. 18, 1989 [DE] Fed. Rep. of Germany ....... 3905087
Jul. 15, 1989 [DE] Fed. Rep. of Germany ....... 3923423

[51] Int. Cl.$^5$ .................................................. C01C 1/24
[52] U.S. Cl. ...................................... 423/545; 208/13; 210/723; 23/302 A
[58] Field of Search ............... 423/527, 540, 545, 550; 526/341; 210/703, 723; 208/13; 23/302 A

[56] References Cited

U.S. PATENT DOCUMENTS 3,408,157 10/1968 Miller et al. .......................... 423/550
3,902,859 9/1975 Greco .................................. 423/545

FOREIGN PATENT DOCUMENTS 0126058 11/1984 European Pat. Off. .
446468 12/1974 U.S.S.R. ............................ 423/545

OTHER PUBLICATIONS

Chemical Abstracts, vol. 88, 1978, paragraph No. 123360s, Columbus, Ohio, US: & JP-A-52 153 899 (Ube Industries) 21.12.1977.

Primary Examiner—Gary P. Straub
Assistant Examiner—Timothy C. Vanoy
Attorney, Agent, or Firm—Sprung. Horn, Kramer & Woods

[57] ABSTRACT

The ammonium sulphate contained in tar-rich waste streams from the production of (meth)acrylonitrile can be precipitated out by adding 1 to 30 times the amount by weight of methanol, relative to the water content of the waste stream, and additionally 0.05 to 10% the amount by weight of ammonia, relative to methanol, to such a waste stream at 10°-60° C. and separating off the ammonium sulphate which precipitates out. The waste stream remaining after separating off the ammonium sulphate can, for example, be disposed of as low-sulphur waste-fuel in a combustion chamber.

9 Claims, No Drawings

PROCESS FOR THE REMOVAL OF AMMONIUM SULPHATE FROM TARRICH WASTE STREAMS FROM THE PRODUCTION OF (METH) ACRYLONITRILE this application is a continuation of application Ser. No. 466,174, filed Jan. 17, 1990.

BACKGROUND OF THE INVENTION

The process according to the invention relates to the removal of ammonium sulphate from tar-rich waste streams from the production of (meth)acrylonitrile by adding methanol and ammonia and separating off the ammonium sulphate thus precipitated out. By this means the residual waste stream is substantially freed from its sulphur content.

In an effort to minimize the emission of environmentally unfriendly gases, to which group $SO_2$ also belongs, laws and regulations have been introduced which lay down emission limits. Thus, for example, for the Federal Republic of Germany it is specified in the "Technische Anleiting Luft" (TA Luft) ("Air Pollution Control Regulations") that the $SO_2$ content of the flue gas from incinerator plants may not exceed a value of 100 mg/Nm$^3$. The corresponding limit for oxides of nitrogen ($NO_x$) is 500 mg/Nm$^3$.

Through the use of sulphur-containing (waste-) fuels, flue gas $SO_2$ concentrations of more than 1000 mg/Nm$^3$ are frequently obtained. For this reason, in order to remove the $SO_2$, for example in coal-fired power stations, a flue gas desulphurization is installed as an additional process step, in which, after an extensive scrubbing of the gas, the $SO_2$ is converted to calcium sulphate ($CaSO_4$) using lime. Because of the growing amounts of calcium sulphate being produced, it is becoming increasingly difficult to usefully dispose of it, for example as a component of building materials. Both investment and operating costs (use of lime amongst others) and disposal of calcium sulphate represent a high burden on energy costs (public energy supply) or production costs (industrial power stations).

In order to minimize this expenditure on an environmentally correct disposal, or even to render it unnecessary, the aim should be pursued of either preventing the production of the harmful substances or, if their formation cannot be avoided, carring out their environmentally correct removal at the earliest possible time, i.e. immediately after their production. The process according to the invention achieves such a solution to the problem of the disposal of ammonium sulphate-containing waste streams from the production of (meth)acrylonitrile.

In the production of acrylonitrile or methacrylonitrile by ammoxidation of propylene or i-butene excess ammonia must be removed from the reaction gas. The ammonia is converted to ammonium sulphate by addition of sulphuric acid; this ammonium sulphate either remains in the sulphate liquor or precipitates out as a crystalline slurry to be separated off.

This sulphate liquor also contains the oligomers and polymers which are unavoidable in the production of (meth)acrylonitrile.

Treatment of the mother liquor from the ammonium sulphate crystallization with methanol has already been tried (EP 126 058); the objective here was seen as being the recovery of additional qualitatively satisfactory ammonium sulphate. For this purpose the tar content (oligomers and polymers) should be at most 25%, preferably at most 20%. Consequently a larger quantity in absolute terms of water and ammonium sulphate is present. As a result the amount of methanol necessary for the fundamentally known salt precipitation also increases sharply. Nevertheless, it is not possible to suppress the residual salt content, and thus the residual sulphur content, to such an extent that on combustion of the residual liquor remaining after this operation the $SO_2$ content of the combustion gases satisfies the TA Luft requirements. In the process of this EP 126 058 the ammonium sulphate obtained in this manner is dissolved in crude sulphate liquor and fed again into the main crystallization process, whilst the total residual liquor originating from the methanol treatment (after recovery of the methanol) is fed to an incinerator and increases the load on this.

It has now been found that it is more advantageous to separate the mother liquor from the main crystallization, in the form in which it is obtained after the separation of the ammonium sulphate, for example, as centrifugate, into a tar-rich waste stream and an essentially tar-free mother liquor by allowing it to settle.

This tar-rich waste stream can be separated off from the surface of the sulphate liquor, for example by skimming off, and treated in the process according to the invention. Such waste streams contain between 25 and 80% by of weight of oligomers and/or polymers from the production of (meth)acrylonitrile, typically 30-60% by weight. Since these tar-containing waste streams have stood in contact with the ammonium sulphate liquor, they still contain ammonium sulphate in an amount of 10-30% by weight, typically 15-25% by weight; if such waste streams are disposed of in an incinerator without pretreatment, these waste streams therefore contribute to an increase in the $SO_2$ and $NO_x$ emissions. The remainder, to 100%, of these waste streams is essentially water. Waste streams of the said type are obtained as waste product in an amount of 20-80 kg/t of (meth)acrylonitrile, typically 25-40 kg/t.

The mother liquor, which for example, has been liberated by skimming off, is fed back into the main crystallization process.

The process according to the invention now makes it possible to remove virtually the entire sulphur content and additionally the major part of the nitrogen content from such waste streams and thus makes these waste streams easier to handle during their disposal.

SUMMARY OF THE INVENTION

A process has been found for the removal of ammonium sulphate from tar-rich waste streams from the production of (meth)acrylonitrile, which is characterized in that 1 to 30 times the amount by weight of methanol, relative to the water content of the waste stream and 0.05-10% by weight of ammonia, relative to the amount of methanol, are added to such waste streams at 10°-60° C., and the ammonium sulphate which precipitates out is separated off.

DETAILED DESCRIPTION OF THE INVENTION

Methanol is used in 1 to 30 times the amount by weight, preferably 3 to 20 times the amount by weight, relative to the water contained in the waste stream.

Ammonia is added to the waste stream in an amount of 0.05-10% by weight, relative to the amount of methanol. Ammonia is preferably added in 0.1-8% the amount by weight, particularly preferrably in 0.2-6% the amount by weight, relative to methanol. This addition can be effected by introduction of gaseous or liquid ammonia or by addition of water containing ammonia. The gaseous ammonia or water containing ammonia can also be waste streams from the production of (meth-)acrylonitrile or suitable waste streams from another production process. The role of the ammonia corresponds to a concept in which the oligomers and polymers are "opened up", possibly by solvation, by which means the occlusion and excessive retention of ammonium sulphate is prevented. In addition, the proportion of polymers in the precipitated ammonium sulphate can be minimized by the addition of ammonia.

The process according to the invention is carried out at 10° to 60° C., preferably at 25° to 45° C. The process can be carried out batchwise or continuously, preferably continuously, in a holding vessel, a flow tube or other reaction equipment familiar to those skilled in the art. The residence times for the crystallization and deposition of the ammonium sulphate to be separated off should be at least 0.1 min. and do not need to exceed 50 min. For the continuous process residence times of 5 to 50 min. are suitable. The process according to the invention is carried out independently of the external pressure. It can therefore be carried out at normal pressure, elevated or reduced pressure. In order to simplify the process and the reaction equipment the process is generally carried out at normal pressure.

After the tar-rich waste stream has been brought into contact with the methanol and the ammonia, the ammonium sulphate which has precipitated out is separated off in a suitable manner, such as filtration, centrifuging off, decanting off, or similar suitable operations, and freed from adhering water, methanol and ammonia in a drier. After this operation this ammonium sulphate can be fed into the ammonium sulphate part of the (meth)acrylonitrile production unit as solid material or as a slurry in water. The ammonium sulphate obtained according to the invention has a high degree of purity, which makes a large number of uses possible, for example as fertilizer or as fertilizer component.

The waste stream remaining after separating off ammonium sulphate is a homogeneous liquid phase. It can be disposed of in a suitable manner, for example by means of extensive evaporation and delivery of the residue to a disposal site or, in a preferred manner, by burning as a low-sulphur waste-fuel in a suitable combustion chamber. If such a waste stream has a sufficiently high calorific value it can even be used profitably in a power station. Before disposal by one of the said methods, other waste streams, for example from the production of (meth)acrylonitrile, can also be added to the ammonium sulphate-free waste stream which is obtained according to the invention.

In a further embodiment of the process according to the invention the waste stream remaining after separating off the ammonium sulphate which has precipitated out is fed into a distillation column, where it is freed from methanol, which is collected as the top product. At the same time the ammonia present escapes from the top and is to be found in the condensed methanol. This condensed methanol containing ammonia is preferably recycled, i.e. used again for the precipitation of ammonium sulphate according to the invention. Where appropriate methanol and ammonia need only be replaced in amounts equivalent to their unavoidable losses. In order to keep the bottom circulation of such a distillation column homogeneous, flowable and thus pumpable, water is advantageously added to the bottom circulation in such an amount that the water content of the bottom circulation is 10-50% by weight of the total bottom circulation. It has proved particularly advantageous if this water to be added contains ammonia. This ammonia content of the water to be added is 0.1-2% by weight of the water to be added and is largely also removed from the top, before the residual waste stream circulating at the bottom is finally withdrawn for disposal. The water, preferably containing ammonia, to be added to the bottom circulation can be a suitable aqueous product stream or waste stream from the (meth)acrylonitrile production unit. Such product streams and waste streams are known to those skilled in the art and familiar with (meth)acrylonitrile production. This addition to the bottom circulation of the said distillation column thus offers a further possibility for the combination of waste streams and thus their simplified disposal.

During continuous process operation, a portion which is substantially freed from methanol and substantially freed from ammonia is continuously removed from the bottom circulation. It is disposed of in the manner described above. Since this waste stream removed from the bottom circulation had not only previously been freed from ammonium sulphate, and thus from the $SO_2$ source, but was also substantially freed from ammonia during the distillation, it constitutes a waste-fuel which is not only low in sulphur, but also low in nitrogen. Its preferred disposal is therefore combustion in a suitable combustion chamber, for example by supplying to a power station. If necessary, such a waste stream can be concentrated, and thus freed from some of its water, before combustion.

The removal of the ammonium sulphate from the waste stream to be treated in accordance with the invention is successful at least to 95%, in many cases to more than 98% up to 99% of the original value. In the combustion of the waste stream treated in accordance with the invention, the $SO_2$ concentration in the flue gas is under 100 mg/$Nm^3$.

EXAMPLES 1 to 28

Ammonium sulphate-containing tar from the acrylonitrile production, methanol and ammonia are added together, in the amounts and compositions indicated in the table, in an open 250 ml glass beaker, with stirring.

The solid precipitated at the particular temperatures was filtered off, dried and analysed, as was the filtrate. The degree of disulpherization was determined for the ammonium sulphate precipitate from the mass balance data.

TABLE $(NH_4)_2SO_4$ removal (Examples 1 to 28)

| | | Example No. | | | | | |
|---|---|---|---|---|---|---|---|
| | | 1 | 2 | 3 | 4 | 5 | 6 |
| Tar used | g | 50 | 50.1 | 50.98 | 52.21 | 50.22 | 50.64 |
| S content of tar | % | 6.055 | 6.055 | 6.055 | 3.032 | 3.032 | 3.032 |
| Ammonium sulphate (theoretical) | g | 12.48 | 12.50 | 12.72 | 6.52 | 6.28 | 6.33 |

TABLE-continued (NH$_4$)$_2$SO$_4$ removal (Examples 1 to 28)

| | | Example No. | | | | | |
|---|---|---|---|---|---|---|---|
| | | 1 | 2 | 3 | 4 | 5 | 6 |
| Water in original tar | % | 34.88 | 34.88 | 34.88 | 20.46 | 20.46 | 20.46 |
| Water in tar used | % | 34.88 | 34.88 | 34.88 | 20.46 | 20.46 | 20.46 |
| Polymer in original tar | % | 40.17 | 40.17 | 40.17 | 67.05 | 67.05 | 67.05 |
| Polymer in tar used | % | 40.17 | 40.17 | 40.17 | 67.05 | 67.05 | 67.05 |
| Methanol/tar | | 1 | 2 | 3 | 2 | 3 | 4 |
| Methanol/polymer | | 2.5 | 5.0 | 7.5 | 3.0 | 4.5 | 6.0 |
| Methanol/water | | 3 | 6 | 9 | 10 | 15 | 20 |
| Proportion of NH$_3$ in methanol | % | 0.5 | 0.5 | 0.5 | 0.1 | 0.1 | 0.1 |
| Methanol temperature | °C. | 20 | 20 | 20 | 20 | 20 | 20 |
| Mixture temperature | °C. | 30 | 30 | 30 | 30 | 30 | 30 |
| Amount of sulphur in filtrate | g | 0.091 | 0.037 | 0.031 | 0.084 | 0.063 | 0.069 |
| Separated ammonium sulphate + polymer | g | 13.09 | 13.95 | 15.69 | 21.72 | 22.04 | 22.42 |
| S removal, relative to original tar | % | 96.98 | 98.77 | 99.01 | 94.72 | 95.88 | 95.49 |

| | | 7 | 8 | 9 | 10 | 11 | 12 |
|---|---|---|---|---|---|---|---|
| Tar used | g | 50.22 | 50.54 | 25.43 | 23 | 10.38 | 5.03 |
| S content of tar | % | 3.032 | 3.032 | 3.032 | 3.032 | 3.032 | 3.032 |
| Ammonium sulphate (theoretical) | g | 6.28 | 6.32 | 3.18 | 2.87 | 1.30 | 0.63 |
| Water in original tar | % | 20.46 | 20.46 | 20.46 | 20.46 | 20.46 | 20.46 |
| Water in tar used | % | 20.46 | 39.21 | 51.37 | 63.53 | 75.67 | 87.84 |
| Polymer in original tar | % | 67.05 | 67.05 | 67.05 | 67.05 | 67.05 | 67.05 |
| Polymer in tar used | % | 67.05 | 51.24 | 41.00 | 30.74 | 20.51 | 10.25 |
| Methanol/tar | | 3 | 3 | 3 | 3 | 3 | 3 |
| Methanol/polymer | | 4.5 | 5.9 | 7.3 | 9.8 | 14.6 | 29.3 |
| Methanol/water | | 15 | 8 | 6 | 5 | 4 | 3 |
| Proportion of NH$_3$ in methanol | % | 0.1 | 0.1 | 0.1 | 0.1 | 0.1 | 0.1 |
| Methanol temperature | °C. | 20 | 20 | 20 | 20 | 20 | 20 |
| Mixture temperature | °C. | 30 | 30 | 30 | 30 | 30 | 30 |
| Amount of sulphur in filtrate | g | 0.063 | 0.124 | 0.074 | 0.115 | 0.098 | 0.110 |
| Separated ammonium sulphate + polymer | g | 22.04 | 17.85 | 7.82 | 6.96 | 2.47 | 0.93 |
| S removal, relative to original tar | % | 95.88 | 91.92 | 90.40 | 83.48 | 68.96 | 27.77 |

| | | 13 | 14 | 15 | 16 | 17 | 18 |
|---|---|---|---|---|---|---|---|
| Tar used | g | 50 | 50 | 50.98 | 50.9 | 50.66 | 50 |
| S content of tar | % | 6.055 | 6.055 | 6.055 | 6.055 | 5.443 | 5.443 |
| Ammonium sulphate (theoretical) | g | 12.48 | 12.48 | 12.72 | 12.60 | 11.36 | 11.22 |
| Water in original tar | % | 34.88 | 34.88 | 34.88 | 34.88 | 39.44 | 39.44 |
| Water in tar used | % | 34.88 | 34.88 | 34.88 | 34.88 | 39.44 | 39.44 |
| Polymer in original tar | % | 40.17 | 40.17 | 40.17 | 40.17 | 38.13 | 38.13 |
| Polymer in tar used | % | 40.17 | 40.17 | 40.17 | 40.17 | 38.13 | 38.13 |
| Methanol/tar | | 3 | 3 | 3 | 3 | 3 | 3 |
| Methanol/polymer | | 7.5 | 7.5 | 7.5 | 7.5 | 7.9 | 7.9 |
| Methanol/water | | 9 | 9 | 9 | 9 | 8 | 8 |
| Proportion of NH$_3$ in methanol | % | 0.5 | 0.5 | 0.5 | 0.5 | 0.5 | 0.5 |
| Methanol temperature | °C. | 2 | 10 | 20 | 30 | 2 | 10 |
| Mixture temperature | °C. | 22 | 27 | 30 | 40 | 24 | 28 |
| Amount of sulphur in filtrate | g | 0.037 | 0.043 | 0.031 | 0.036 | 0.038 | 0.036 |
| Separated ammonium sulphate + polymer | g | 23.2 | 15.29 | 15.69 | 14.73 | 16.27 | 15.83 |
| Polymer in separated salt | % | 46.88 | 19.55 | 19.72 | 15.46 | 31.11 | 30.08 |
| S removal, relative to original tar | % | 98.78 | 98.59 | 99.01 | 98.82 | 98.63 | 98.69 |

| | | 19 | 20 | 21 | 22 | 23 | 24 |
|---|---|---|---|---|---|---|---|
| Tar used | g | 50.35 | 50.22 | 55.3 | 50 | 50.98 | 50.15 |
| S content of tar | % | 5.443 | 5.443 | 5.443 | 6.055 | 6.055 | 6.055 |
| Ammonium sulphate (theoretical) | g | 11.29 | 11.27 | 12.40 | 12.48 | 12.72 | 12.51 |
| Water in original tar | % | 39.44 | 39.44 | 39.44 | 34.88 | 34.88 | 34.88 |
| Water in tar used | % | 39.44 | 39.44 | 39.44 | 34.88 | 34.88 | 34.88 |
| Polymer in original tar | % | 38.13 | 38.13 | 38.13 | 40.17 | 40.17 | 40.17 |
| Polymer in tar used | % | 38.13 | 38.13 | 38.13 | 40.17 | 40.17 | 40.17 |
| Methanol/tar | | 3 | 3 | 3 | 3 | 3 | 3 |
| Methanol/polymer | | 7.9 | 7.9 | 7.9 | 7.5 | 7.5 | 7.5 |
| Methanol/water | | 8 | 8 | 8 | 9 | 9 | 9 |
| Proportion of NH$_3$ in methanol | % | 0.5 | 0.5 | 0.5 | 1 | 0.5 | 0.25 |
| Methanol temperature | °C. | 21 | 30 | 40 | 20 | 20 | 20 |
| Mixture temperature | °C. | 35 | 42 | 50 | 30 | 34 | 30 |
| Amount of sulphur in filtrate | g | 0.039 | 0.032 | 0.056 | 0.034 | 0.031 | 0.030 |
| Separated ammonium sulphate + polymer | g | 14.59 | 15.08 | 19.11 | 14.65 | 15.69 | 15.69 |
| Polymer in separated salt | % | 23.70 | 26.16 | 36.29 | 15.78 | 19.72 | 21.02 |
| S removal, relative to original tar | % | 98.56 | 98.84 | 98.15 | 98.88 | 99.01 | 99.03 |

| | | 25 | 26 | 27 | 28 |
|---|---|---|---|---|---|
| Tar used | g | 50 | 50 | 50 | 50 |
| S content of tar | % | 6.055 | 5.071 | 3.071 | 5.071 |
| Ammonium sulphate (theoretical) | g | 12.48 | 10.45 | 10.45 | 10.45 |
| Water in original tar | % | 34.88 | 49.64 | 49.64 | 49.46 |
| Water in tar used | % | 34.88 | 53.8 | 60.35 | 65.27 |
| Polymer in original tar | % | 40.17 | 28.46 | 28.46 | 28.46 |
| Polymer in tar used | % | 40.17 | 26.11 | 22.41 | 19.63 |
| Methanol/tar | | 3 | 2.8 | 2.4 | 2.2 |
| Methanol/polymer | | 7.5 | 11.6 | 13.8 | 16.0 |

TABLE-continued

$(NH_4)_2SO_4$ removal (Examples 1 to 28)

| | | Example No. | | | |
|---|---|---|---|---|---|
| | | 9 | 6 | 5 | 5 |
| Methanol/water | | 9 | 6 | 5 | 5 |
| Proportion of $NH_3$ in methanol | % | 0.1 | 1 | 3 | 5 |
| Methanol temperature | °C. | 20 | 20 | 20 | 20 |
| Mixture temperature | °C. | 30 | 30 | 30 | 30 |
| Amount of sulphur in filtrate | g | 0.032 | 0.033 | 0.057 | 0.072 |
| Separated ammonium sulphate + polymer | g | 17.13 | 13.22 | 13.15 | 13.16 |
| Polymer in separated salt | % | 27.92 | 21.96 | 22.31 | 22.85 |
| S removal, relative to original tar | % | 98.96 | 98.71 | 97.76 | 97.17 |

EXAMPLE 29

700 kg of tar, containing 7.4% sulphur, at 70° C. from the acrylonitrile production, 2480 kg of methanol and 40 kg of aqueous ammonia (25% strength) were mixed together, with stirring, in a 5 m³ stirred vessel. The ammonium sulphate was precipitated out centrifuged off and dried. The runoff from the centrifuge contained 0.99% of the original amount of sulphur.

The moist salt having a total moisture of 43.25% (methanol: $H_2O$ ratio about 3:1) could be dried in a drier down to a total moisture of 2–4%. No further methanol could be detected in the dried ammonium sulphate.

The degree of desulphurization of the tar was about 99%.

EXAMPLE 30

2000 g of hot tar, containing ammonium sulphate, (70° C.) from the acrylonitrile production having a sulphur content of 4.7% by weight were stirred into 6000 g of methanol and 24 g $NH_3$ water (25% strength) in a 10 l glass container. The solid precipitated out during this mixing was filtered, washed with a little methanol and dried. 450 g of ammonium sulphate were obtained.

The filtrate (6902 g) still contained 1,712 g of sulphur, so that the degree of desulphurization was 98.18%.

6700 g of the filtrate were mixed with 2523 g of a water quench stream containing polymer (30% by weight) from the acrylonitrile production and continuously distilled up in a packed column 1500 mm in length and 30 mm in diameter with a circulation reboiler and top condensation (coolant at 4°–5° C.).

The product feed containing 61% by weight methanol was pumped into the column at a rate of 547 g/hour at a height of 50 mm. At a reflux ratio of 3:1, 311 g/hour of top product at 66° C. and 220 g/hour of bottom product at 102° C. were removed. The bottom product was readily pumpable at a viscosity of 0.93 mPas (90° C.) and still contained 0.25% by weight residual methanol.

What is claimed is:

1. A process for the removal of ammonium sulphate from the tar-rich waste phase separated from the mother liquor from the main crystallization of $NH_4SO_4$ in the treatment of the $NH_4SO_4$ tar waste stream from the production of (meth)acrylonitrile, said phase having a tar content of between 25 and 80% by weight, to remove at least 95% of the ammonium sulphate from said phase, where 1 to 30 times the amount by weight of methanol, relative to the water content of the said phase, and 0.2–6% by weight of ammonia, relative to the amount of methanol, are added to said phase, the process is carried out at a temperature of 25°–45° C. and the ammonium sulphate which precipitates out is separated off.

2. The process of claim 1, wherein 3 to 20 times the amount by weight of methanol is used.

3. The process of claim 1, wherein the waste stream remaining after separating off the ammonium sulphate is fed to a combustion chamber as low-sulphur waste-fuel.

4. The process of claim 1, wherein the methanol is distilled off from the water phase remaining after separating off the ammonium sulphate, together with the ammonia.

5. The process of claim 4, wherein the methanol, containing ammonia, which is distilled off is used again for the removal of ammonium sulphate from the waste phase.

6. The process of claim 4, wherein the bottom stream from the methanol distillation is kept flowable by addition of water.

7. The process of claim 4, wherein the waste stream remaining after the methanol distillation is fed into a combustion chamber as a low-sulphur and low-nitrogen waste-fuel.

8. The process of claim 1, carried out continuously.

9. The process of claim 4, wherein the bottom stream from the methanol distillation is kept flowable by the addition of water containing ammonia.

* * * * *